United States Patent
Wang et al.

(10) Patent No.: US 10,772,501 B2
(45) Date of Patent: Sep. 15, 2020

(54) METHOD AND ELECTRONIC DEVICE FOR POSITIONING EYEBALL IN RETINOPATHY IMAGE

(71) Applicant: BOE TECHNOLOGY GROUP CO., LTD., Beijing (CN)

(72) Inventors: Lvwei Wang, Beijing (CN); Zhenglong Li, Beijing (CN); Hui Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/013,898

(22) Filed: Jun. 20, 2018

(65) Prior Publication Data

US 2019/0059719 A1    Feb. 28, 2019

(30) Foreign Application Priority Data

Aug. 22, 2017 (CN) .......................... 2017 1 0723062

(51) Int. Cl.
| | |
|---|---|
| A61B 3/14 | (2006.01) |
| G06T 7/00 | (2017.01) |
| G06K 9/00 | (2006.01) |
| G06T 7/70 | (2017.01) |
| G06K 9/62 | (2006.01) |
| G06K 9/46 | (2006.01) |
| G06N 3/08 | (2006.01) |
| G06N 3/04 | (2006.01) |

(52) U.S. Cl.
CPC ............ *A61B 3/14* (2013.01); *G06K 9/00604* (2013.01); *G06K 9/4628* (2013.01); *G06K 9/6274* (2013.01); *G06N 3/0454* (2013.01); *G06N 3/08* (2013.01); *G06T 7/0014* (2013.01); *G06T 7/70* (2017.01); *G06K 2209/05* (2013.01); *G06T 2207/10004* (2013.01); *G06T 2207/20081* (2013.01); *G06T 2207/20084* (2013.01); *G06T 2207/30041* (2013.01)

(58) Field of Classification Search
CPC ..................... A61B 3/14; G06T 7/0014; G06T 2207/30041; G06T 2207/20084; G06T 2207/20081; G06T 2207/10004; G06K 9/00604; G06K 2209/05
See application file for complete search history.

(56) References Cited

U.S. PATENT DOCUMENTS

| | | | |
|---|---|---|---|
| 2017/0188823 | A1 | 7/2017 | Ganesan et al. |
| 2018/0018451 | A1* | 1/2018 | Spizhevoy ......... G06K 9/00617 |
| 2019/0110753 | A1* | 4/2019 | Zhang .................. A61B 5/7267 |

FOREIGN PATENT DOCUMENTS

| | | |
|---|---|---|
| CN | 104766059 A | 7/2015 |
| CN | 106778567 A | 5/2017 |

OTHER PUBLICATIONS

First Chinese Office Action dated Feb. 3, 2020, received for corresponding Chinese Application No. 201710723062.9, 19 pages.

* cited by examiner

*Primary Examiner* — Jack Dinh
(74) *Attorney, Agent, or Firm* — Kinney & Lange, P.A.

(57) ABSTRACT

A method and an electronic device for positioning an eyeball in a retinopathy image are disclosed. The method includes: using retinopathy image data with corresponding labeled data to train a deep learning network based on a loss function, so as to obtain a trained deep learning network; and processing retinopathy image data to be tested by using the trained deep learning network to obtain corresponding eyeball center coordinates and/or an eyeball diameter.

20 Claims, 4 Drawing Sheets

METHOD AND ELECTRONIC DEVICE FOR POSITIONING EYEBALL IN RETINOPATHY IMAGE

CROSS-REFERENCE TO RELATED APPLICATION(S)

This application claims priority to the Chinese Patent Application No. 201710723062.9, filed on Aug. 22, 2017, entitled "METHOD AND ELECTRONIC DEVICE FOR POSITIONING EYEBALL IN RETINOPATHY IMAGE", which is incorporated herein by reference in its entirety.

TECHNICAL FIELD

The present disclosure relates to the field of image processing technology, and in particular, to a method and electronic device for positioning an eyeball in a retinopathy image.

BACKGROUND

Retinopathy is also known as Rieger central retinitis or hemorrhagic macular degeneration of youth. This disease is an isolated exudative chorioretinal lesion that occurs in and around a macula, with subretinal neovascularization and hemorrhage.

For detailed observation of retinopathy, it is generally required to collect retinopathy images for analysis.

SUMMARY

In view of this, one of objectives of embodiments of the present disclosure is to provide a method and an apparatus for positioning an eyeball in a retinopathy image, which may implement the eyeball positioning in the retinopathy image more accurately.

Based on the foregoing objective, a first aspect of an embodiment of the present disclosure provides a method for positioning an eyeball in a retinopathy image, including:

using retinopathy image data with corresponding labeled data to train a deep learning network based on a loss function, so as to obtain a trained deep learning network; and processing retinopathy image data to be tested by using the trained deep learning network to obtain at least one of corresponding eyeball center coordinates and an eyeball diameter.

Optionally, the using the retinopathy image data with the corresponding labeled data to train the deep learning network based on the loss function so as to obtain the trained deep learning network includes: inputting the retinopathy image data to the deep learning network to obtain corresponding prediction data; comparing the labeled data with the prediction data based on the loss function to obtain a comparison result; adjusting parameters in the deep learning network according to the comparison result; and repeating the above steps until the comparison result reaches a preset threshold, so as to obtain the trained deep learning network.

Optionally, the method further includes: acquiring the retinopathy image data; and performing data labeling on the retinopathy image data to obtain the labeled data.

Optionally, the method for the retinopathy image further includes:
performing data preprocessing on the retinopathy image data to obtain the preprocessed retinopathy image data, wherein the performing the data labeling on the retinopathy image data to obtain the labeled data includes:
performing data labeling on the preprocessed retinopathy image data to obtain the labeled data.

Optionally, the performing the data preprocessing on the retinopathy image data includes at least one of:
performing image augmentation on the retinopathy image data, and
oversampling the retinopathy image data.

Optionally, the performing the image augmentation on the retinopathy image data includes:
performing the image augmentation by one or more of: random tailoring, rotating, flipping, scaling, brightness adjustment, and contrast adjustment.

Optionally, the performing the data labeling on the retinopathy image data includes:
performing the data labeling by manual labeling or by a combination of image processing and manual screening.

Optionally, the deep learning network is selected from an Inception-ResNet model or a GoogLeNet v3 model.

Optionally, the loss function is:

$$L(u, v) = \Sigma_{i=\{x,y,d\}} \text{Smooth}_{L1}(u_i, v_i);$$

$$\text{Smooth}_{L1}(z) = \begin{cases} 0.5\, z^2, & z < 1 \\ |z| - 0.5, & z \geq 1 \end{cases};$$

wherein $v=(v_x,v_y,v_d)$ is the labeled data, $u=(u_x,u_y,u_d)$ is prediction data output by the deep learning network which corresponds to the labeled data; $v_x,v_y$ are the respective labeled eyeball center coordinates, $v_d$ is the labeled eyeball diameter; $u_x,u_y$ are the respective eyeball center coordinates output by the deep learning network, $u_d$ is the eyeball diameter output from the deep learning network, and z is the difference between the prediction data and the labeled data.

Optionally, the adjusting the parameter in the deep learning network according to the comparison result includes:
adjusting a learning rate and/or a momentum of the deep learning network.

A second aspect of an embodiment of the present disclosure further provides an eyeball positioning apparatus for a retinopathy image, including:
a model establishment module, configured to use retinopathy image data with corresponding labeled data to train a deep learning network based on a loss function, so as to obtain a trained deep learning network; and
an eyeball positioning module, configured to process retinopathy image data to be tested by using the trained deep learning network to obtain corresponding eyeball center coordinates and/or an eyeball diameter.

A third aspect of an embodiment of the present disclosure further provides an electronic device, including:
a processor; and
a memory storing instructions which, when executed by the processor, cause the processor to perform any of the methods as described above.

A fourth aspect of an embodiment of the present disclosure further provides a computer readable storage medium storing instructions, which, when executed by a processor, cause the processor to perform any of the methods as described above.

DETAILED DESCRIPTION

In order to make the objectives, technical solutions, and advantages of the present disclosure clearer, the present disclosure will be described in detail in conjunction with particular embodiments and with reference to the accompanying drawings.

It should be noted that all expressions using "first" and "second" in the embodiments of the present disclosure are intended to distinguish between two different entities or parameters with the same names. Thus, "first" and "second" are used for convenience of description only, but should not be understood as limitations on the embodiments of the present disclosure, which will not be noted to subsequent embodiments any more.

In a process of implementing the present disclosure, it is found that there are at least problems as follows in the prior art.

Currently, a retinopathy image does not have a high quality. When conventional methods are used to locate an eyeball or an eyeball region, it is often affected by factors such as a low resolution, a too low brightness, interference from a camera's light spot, resulting in inaccurate eyeball positioning.

Figure 1:
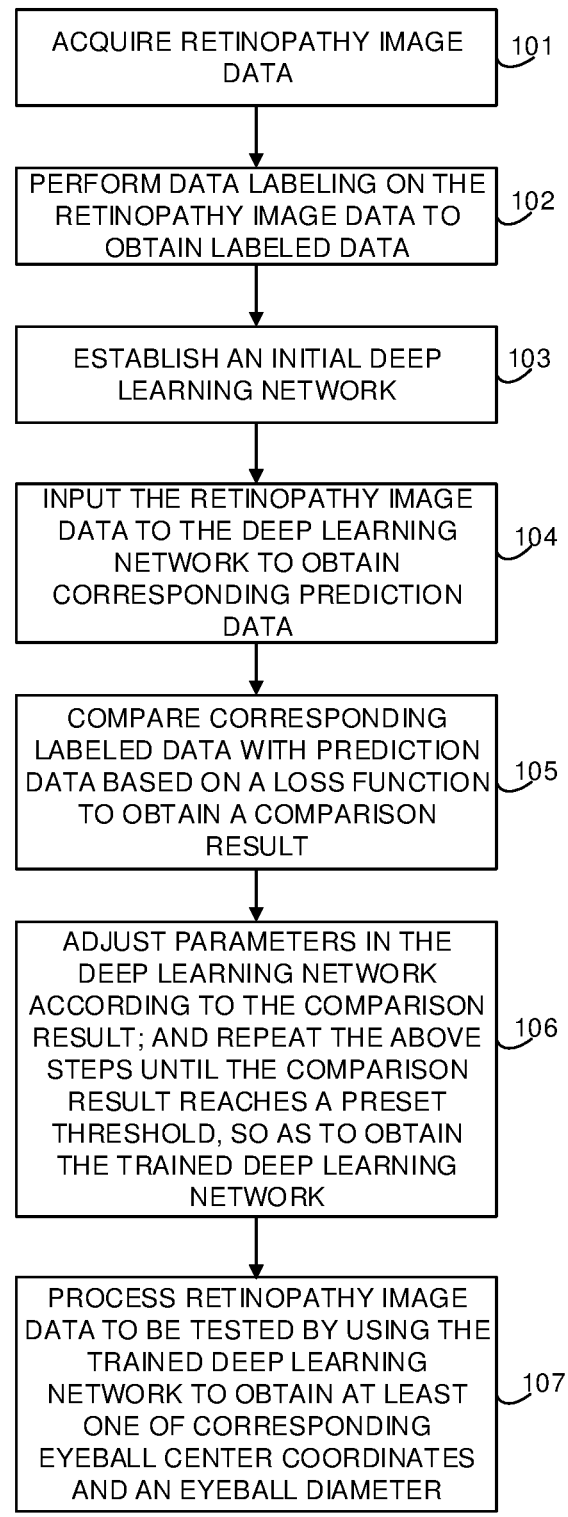
FIG. 1 shows an exemplary flowchart of a method for positioning an eyeball in a retinopathy image according to an embodiment of the present disclosure.

According to some embodiments of the present disclosure, there is provided an embodiment of a method for positioning an eyeball in a retinopathy image, which may implement eyeball positioning on the retinopathy image more accurately. As shown in FIG. 1, it is a schematic flowchart of an embodiment of a method for positioning an eyeball in the retinopathy image provided by the present disclosure.

The method for positioning an eyeball in the retinopathy image includes steps as follows.

In Step 101, retinopathy image data are acquired; and optionally, the amount of the retinopathy image data here should be as much as possible in order to make a finally established deep learning network model accurate enough.

In Step 102, data labeling is performed on the retinopathy image data to obtain labeled data; wherein the labeled data include at least one of eyeball center coordinates and an eyeball diameter labeled.

It should be noted that both Step 101 and Step 102 are optional. Since in some embodiments, the retinopathy image data may be stored locally or generated, without being acquired from externally. In addition in some embodiments, the retinopathy image data themselves may have labeled data, without being labeled manually. For example, the labeled data may be generated by automatic detection of a collection device when the retinopathy image is collected. In other words, the above two steps are not necessary steps in the eyeball positioning method.

In an optional Step 103, an initial deep learning network is established; optionally, the initial deep learning network may be selected from a latest CNN (Convolutional Neural Network) model, such as an Inception-ResNet model or a GoogLeNet v3 model or any of these models being modified appropriately. However in other embodiments, the deep learning network may also be a trained deep learning network, such as a preliminarily trained deep learning network provided by a third party.

Next in some embodiments, the deep learning network may be trained based on a loss function using the retinopathy image with corresponding labeled data, so as to obtain a trained deep learning network. More specifically, in some embodiments, this step may include Steps 104-106 as follows.

Step 104, in which the retinopathy image data are input to the deep learning network to obtain corresponding prediction data;

Step 105, in which the corresponding label data and the prediction data are compared based on the loss function to obtain a comparison result;

Step 106, in which parameters in the deep learning network are adjusted according to the comparison result, and the above steps are repeated until the comparison result reaches a preset threshold to obtain the trained deep learning network; here, the preset threshold is set according to accuracy required by the deep learning network, a specific value of which is not limited;

Finally in Step 107, retinopathy image data to be tested is processed by using the trained deep learning network to obtain at least one of the corresponding eyeball center coordinates and the eyeball diameter.

As can be seen from the above embodiment, the method for positioning an eyeball in the retinopathy image provided by the embodiment of the present disclosure uses the deep learning method to determine at least one of the eyeball center coordinates and the eyeball diameter in the retinopathy image, so as to learn a position and an area of the eyeball, which has a stronger anti-interference ability and a higher precision compared to the traditional methods, and thus may be used for further pre-processing a task, such as a computer aided diagnosis.

Figure 2:
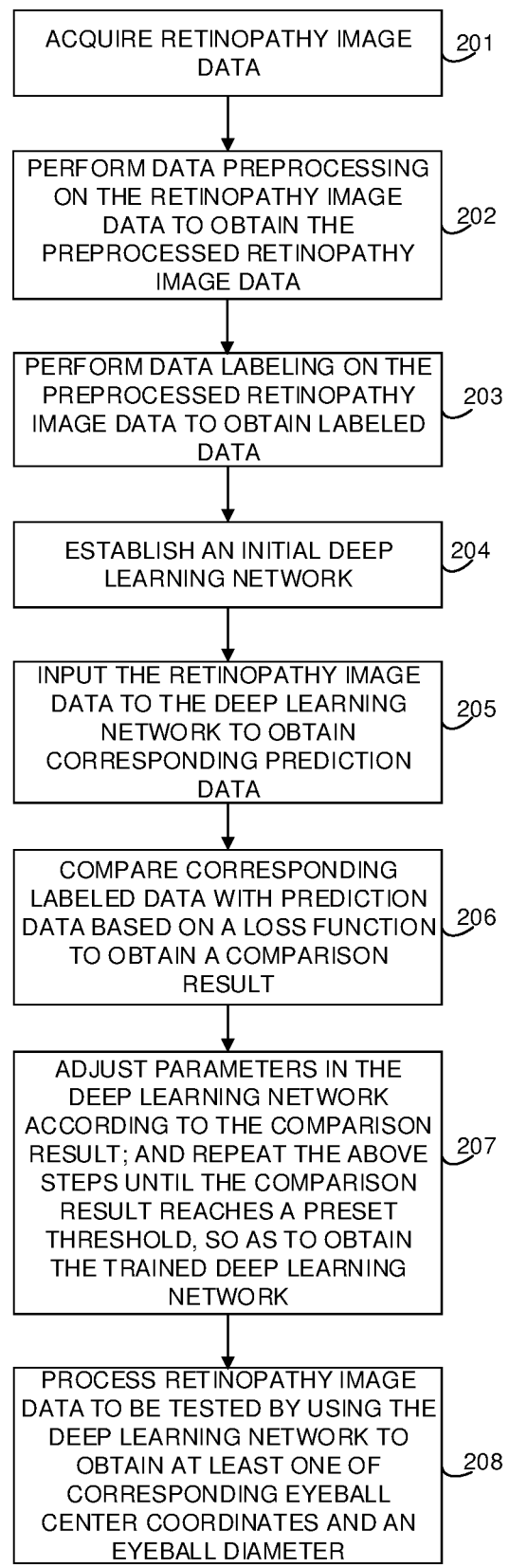
FIG. 2 shows an exemplary flowchart of a method for positioning an eyeball in a retinopathy image according to another embodiment of the present disclosure.

An embodiment of the present disclosure also provides another embodiment of a method for positioning an eyeball in a retinopathy image, which may implement the eyeball positioning on the retinopathy image more accurately. As shown in FIG. 2, it shows an exemplary flowchart of a method for positioning an eyeball in a retinopathy image according to another embodiment of the present disclosure.

The method for positioning an eyeball in the retinopathy image includes steps as follows.

In Step 201, retinopathy image data are acquired; and optionally, the amount of the retinopathy image data here should be as much as possible in order to make a finally established deep learning network model accurate enough.

In order to avoid influence of data quality and data imbalance on training accuracy, data preprocessing is performed first. Therefore in Step 202, data preprocessing is performed on the retinopathy image data to obtain the preprocessed retinopathy image data.

Optionally, the data preprocessing includes:

performing image augmentation on the retinopathy image data; optionally, performing the image augmentation by using one or more of random tailoring, rotating, flipping, scaling, brightness adjustment, and contrast adjustment;

and/or performing an over-sampling process on the retinopathy image data, so that for the imbalanced data, a small number of samples may be multiplied by means of the over-sampling process.

Figure 3:
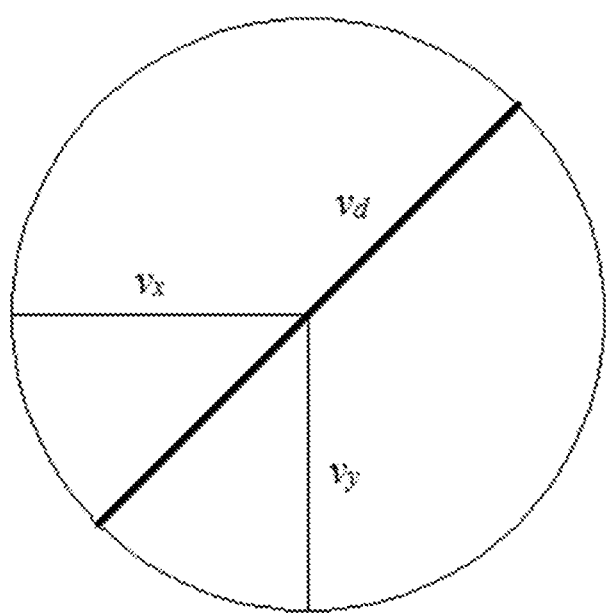
FIG. 3 shows a schematic diagram of a labeled eyeball image in an embodiment of a method for positioning an eyeball in a retinopathy image according to an embodiment of the present disclosure.

In Step 203, data labeling may be performed on the preprocessed retinopathy image data to obtain the labeled data; wherein, the labeled data include labeled eye center coordinates ($v_x$, $v_y$) and an eyeball diameter $v_d$; optionally, the data labeling may be performed by manual labeling, or by a combination of image processing and manual screening, as shown in FIG. 3.

In Step 204, an initial deep learning network is established; optionally, reference may be made to recent CNN models, such as an Inception-ResNet, GoogLeNet v3, for modification; or a CNN network may be built up for training and prediction.

It should be noted that similar to Steps 101 to 103, Steps 201 to 204 are also optional steps.

Next, in some embodiments, the deep learning network can be trained based on a loss function using the retinopathy image data having corresponding labeled data to obtain the trained deep learning network. More specifically, in some embodiments, this step may include Steps 205-207 as follows.

In Step 205, the retinopathy image data are input to the deep learning network to obtain corresponding prediction data; the retinopathy image data are input to the initial deep learning network, the output of the initial deep learning network is the prediction data of the retinopathy image data, and the prediction data include predicted eye center coordinates ($u_x$, $u_y$) and/or a predicted eyeball diameter $u_d$.

In Step 206, the corresponding labeled data and the prediction data are compared based on the loss function to obtain a comparison result. In this way, the initial deep learning network automatically compares the prediction data with the labeled data to train parameters of the initial deep learning network. A comparison standard is referred to as a loss function. Optionally, the loss function of the eyeball circle labeled area may be:

$$L(u, v) = \Sigma_{i=\{x,y,d\}} \text{Smooth}_{L1}(u_i, v_i);$$

$$\text{Smooth}_{L1}(z) = \begin{cases} 0.5\ z^2, z < 1 \\ |z| - 0.5, z \geq 1 \end{cases};$$

wherein, $v=(v_x,v_y,v_d)$ is the labeled data, $u=(u_x,u_y,u_d)$ is prediction data output by the deep learning network which corresponds to the labeled data; $v_x,v_y$ are the respective labeled eyeball center coordinates, $v_d$ is the labeled eyeball diameter; $u_x,u_y$ are the respective eyeball center coordinates output by the deep learning network, $u_d$ is the eyeball diameter output from the deep learning network, and z is the difference between the prediction data and the labeled data.

In Step 207, the parameters of the deep learning network are adjusted according to the comparison result, and the above steps are repeated until the comparison result reaches a preset threshold to obtain the trained deep learning network. Here, the preset threshold is set according to the accuracy required by the deep learning network, and a specific value thereof is not particularly limited herein. Optionally, the adjusting the parameters in the initial deep learning network includes: adjusting a learning rate and/or a momentum of the initial deep learning network. As such, the parameters, such as the learning rate, the momentum, are repeatedly adjusted to be optimized, in order to improve the model accuracy and optimize the prediction accuracy.

Finally in Step 208, retinopathy image data to be tested is processed by using the trained deep learning network to obtain the corresponding eyeball center coordinates and/or the eyeball diameter.

As can be seen from the above embodiment, the method for positioning an eyeball in the retinopathy image provided by the embodiment of the present disclosure uses the deep learning method to position the eyeball center coordinates and/or the eyeball diameter in the retinopathy image, so as to learn a position and an area of the eyeball, which has a stronger anti-interference ability and a higher precision compared to the traditional methods, and thus may be used for further pre-processing a task, such as a computer aided diagnosis; and the finally generated model being applied as a preprocessing part of a fundus image processing may determine the position and the size of the eyeball effectively.

Figure 4:
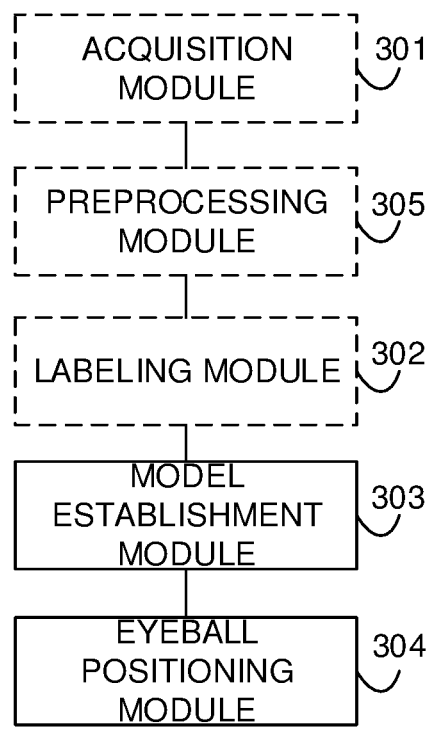
FIG. 4 shows an exemplary schematic diagram of an apparatus for positioning an eyeball in a retinopathy image according to an embodiment of the present disclosure.

In a second aspect of the embodiments of the present disclosure, an embodiment of an eyeball positioning apparatus for a retinopathy image is also provided, which may implement eyeball positioning on the retinopathy image more accurately. As shown in FIG. 4, it is a schematic structure diagram of an eyeball positioning apparatus for a retinopathy image according to an embodiment of the present disclosure.

The eyeball positioning device for the retinopathy image includes:

an acquisition module 301, configured to acquire retinopathy image data;

a labeling module 302, configured to perform data labeling on the retinopathy image data to obtain the labeled data, wherein the labeled data include eyeball center coordinates and/or an eyeball diameter labeled;

a model establishment module 303, configured to train a deep learning network based on a loss function using the retinopathy image with corresponding labeled data, so as to obtain a trained deep learning network. More specifically, the model establishment module 303 may be used for establishing an initial deep learning network; inputting the retinopathy image data to the deep learning network to obtain corresponding prediction data; comparing the labeled data with the prediction data based on the loss function to obtain a comparison result; adjusting parameters in the deep learning network according to the comparison result; and repeating the above steps until the comparison result reaches a preset threshold, so as to obtain the trained deep learning network;

an eyeball positioning module 304, configured to process retinopathy image data to be tested by using the trained deep learning network to obtain corresponding eyeball center coordinates and/or an eyeball diameter.

As can be seen from the above embodiment, the eyeball positioning apparatus for the retinopathy image provided by the embodiment of the present disclosure uses the deep learning method to position the eyeball center coordinates and/or the eyeball diameter in the retinopathy image, so as to learn a position and an area of the eyeball, which has a stronger anti-interference ability and a higher precision compared to the traditional methods, and thus may be used for further pre-processing a task, such as a computer aided diagnosis.

In order to avoid influence of data quality and data imbalance on training accuracy, data preprocessing is performed first. Optionally, the eyeball positioning apparatus for the retinopathy image further includes:

a preprocessing module 305, configured to perform data preprocessing on the retinopathy image data to obtain the preprocessed retinopathy image data;

the labeling module 302, particularly configured to perform data labeling on the preprocessed retinopathy image data to obtain the labeled data.

Optionally, the preprocessing module 305 is particularly configured to:

perform data augmentation on the retinopathy image data; and/or perform an over-sampling process on the retinopathy image data, so that for the imbalanced data, a small number of samples may be multiplied by means of the over-sampling process.

Optionally, the performing the data augmentation on the retinopathy image data includes:

performing the data augmentation by using one or more of random tailoring, rotating, flipping, scaling, brightness adjustment, and contrast adjustment.

Optionally, the labeling module 302 is particularly configured to:

perform the data labeling by manual labeling or by a combination of image processing and manual screening.

Optionally, the deep learning network is selected from an Inception-ResNet model or a GoogLeNet v3 model.

Optionally, the loss function is:

$$L(u, v) = \Sigma_{i=\{x,y,d\}} \text{Smooth}_{L1}(u_i, v_i);$$

$$\text{Smooth}_{L1}(z) = \begin{cases} 0.5\, z^2, z < 1 \\ |z| - 0.5, z \geq 1 \end{cases};$$

wherein $v=(v_x, v_y, v_d)$ is the labeled data, $u=(u_x, u_y, u_d)$ is prediction data output by the deep learning network which corresponds to the labeled data; $v_x, v_y$ are the respective labeled eyeball center coordinates, $v_d$ is the labeled eyeball diameter; $u_x, u_y$ are the respective eyeball center coordinates output by the deep learning network, $u_d$ is the eyeball diameter output from the deep learning network, and z is the difference between the prediction data and the labeled data.

Optionally, the model establishment module 303 is further configured to:

adjust a learning rate and/or a momentum of the deep learning network. As such, the parameters, such as the learning rate, the momentum, are repeatedly adjusted to be optimized, in order to improve the model accuracy and optimize the prediction accuracy.

Figure 5:
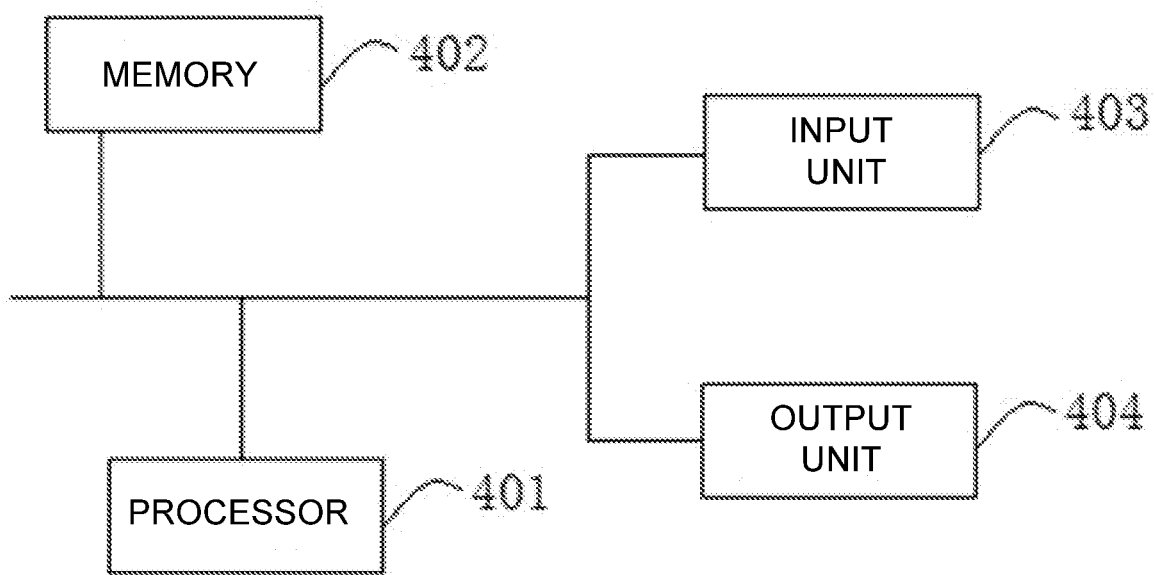
FIG. 5 shows a schematic structure diagram of an electronic device according to an embodiment of the present disclosure.

In a third aspect of the embodiments of the present disclosure, an embodiment of an electronic device for performing the method for positioning an eyeball in the retinopathy image is provided. As shown in FIG. 5, it is a hardware structure schematic diagram of an embodiment of an electronic device for performing the method for positioning an eyeball in the retinopathy image provided by the present disclosure.

As shown in FIG. 5, the electronic device includes:

one or more processors 401 and a memory 402. In FIG. 5, there is one processor 401 shown as an example.

The electronic device for performing the method for positioning an eyeball in the retinopathy image may further include: an input unit 403 and an output unit 404.

The processor 401, the memory 402, the input unit 403, and the output unit 404 may be connected via a bus or by other ways. In FIG. 5, the connection via the bus is taken as an example.

The memory 402, as a non-volatile computer-readable storage medium, may be used to store non-volatile software programs, non-volatile computer-executable programs, and modules, such as program instructions/modules (e.g., the acquisition module 301, the preprocessing module 305, the labeling module 302, the model establishment module 303, and the eyeball positioning module 304 as shown in FIG. 4) corresponding to the method for positioning an eyeball in the retinopathy image in the embodiments of the present disclosure. The processor 401 executes various functional applications and data processing of the server by running non-volatile software programs, instructions, and/or modules stored in the memory 402, i.e., implementing the method for positioning an eyeball in the retinopathy image in the above method embodiments.

The memory 402 may include a program storage region and a data storage region, wherein the program storage region may store an operating system, and an application required by at least one function; the data storage region may store data created according to the use of the eyeball positioning apparatus for the retinopathy image, etc. In addition, the memory 402 may include a high-speed random access memory, and may also include a non-volatile memory, such as at least one disk storage device, a flash memory device, or other non-volatile solid-state storage devices. In some embodiments, the memory 402 optionally includes memories remotely located with respect to the processor 401, which may be connected to a member user behavior monitoring device through the network. Examples of such networks include, but are not limited to, the Internet, intranets, local area networks, mobile communications networks, and combinations thereof.

The input unit 403 may receive input numerical or character information and generate a key signal input related to user setting and function control of the eyeball positioning apparatus for the retinopathy image. The output unit 404 may include a display device, such as a display screen.

The one or more modules are stored in the memory 402. When being executed by the one or more processors 401, the method for positioning an eyeball in the retinopathy image in any of the above method embodiments is performed. The embodiment of the electronic device for performing the method for positioning an eyeball in the retinopathy image has the same or similar technical effects as those of any of the foregoing method embodiments.

The embodiments of the present disclosure also provide a non-transitory computer storage medium. The computer storage medium stores computer-executable instructions. The computer-executable instructions may perform the method for positioning an eyeball in the retinopathy image in any of the above-described method embodiments. The embodiment of the non-transitory computer storage medium has the same or similar technical effects as those of any of the foregoing method embodiments.

Finally, it should be noted that the skilled in the art may understand that all or part of the processes in the foregoing method embodiments may be implemented by instructing related hardware by means of the computer programs, and the programs may be stored in a computer readable storage. When the programs are executed, the programs may include the processes of the above method embodiments. The storage medium may be a disk, an optical disk, a Read-Only Memory (ROM) or a Random Access Memory (RAM) etc. The embodiments of the computer program have the same or similar technical effects as those of any of the foregoing method embodiments.

It should be understood by the skilled in the art that the discussion of any of the above embodiments is merely exemplary and is not intended to suggest that the scope of the disclosure, including the claims, is limited to these examples; under the principle of the present disclosure, technical features in the above embodiments and in different embodiments may also be combined, and steps thereof may be implemented in any order, and there are many other variations of different aspects of the disclosure as described above, which are not provided in details for the sake of conciseness.

In addition, well known power/ground connections to integrated circuit (IC) chips and other components may or may not be shown in the drawings provided for simplicity of illustration and discussion, so as not to obscure the present disclosure. Moreover, the apparatus/device may be shown in a block diagram form in order to avoid obscuring the present disclosure, and this also takes into account the fact that the details regarding the implementation of these block diagram of the apparatuses/devices are highly dependent on the platform on which the present disclosure is to be implemented (i.e., these details should be completely within the understanding of the skilled in the art). Where specific details (e.g., circuitry) are set forth to describe example embodiments of the present disclosure, it will be apparent to the skilled in the art that the present disclosure may be implemented without these specific details or with variations of these specific details. Therefore, these descriptions should be considered as illustrative but not restrictive.

Although the present disclosure has been described in conjunction with the particular embodiments thereof, many alternatives, modifications, and variations of these embodiments will be apparent to the skilled in the art in light of the foregoing description. For example, other memory architectures (e.g., dynamic RAM (DRAM)) may use the embodiments discussed.

The embodiments of the present disclosure are intended to embrace all such alternatives, modifications, and variations that fall within the broad scope of the appended claims. Therefore, any omissions, modifications, equivalent replacements, improvements etc. made within the spirit and principle of the present disclosure should be included in the protection scope of the present disclosure.

We claim:

1. A method for positioning an eyeball in a retinopathy image, the method comprising:
   using retinopathy image data with corresponding labeled data to train a deep learning network based on a loss function, so as to obtain a trained deep learning network; and
   processing retinopathy image data to be tested by using the trained deep learning network, to obtain at least one of corresponding eyeball center coordinates and an eyeball diameter.

2. The method according to claim 1, wherein the using the retinopathy image data with the corresponding labeled data to train the deep learning network based on the loss function so as to obtain the trained deep learning network comprises:
   inputting the retinopathy image data to the deep learning network to obtain corresponding prediction data;
   comparing the labeled data with the prediction data based on the loss function to obtain a comparison result;
   adjusting parameters in the deep learning network according to the comparison result; and
   repeating the steps of inputting, comparing and adjusting until the comparison result reaches a preset threshold, so as to obtain the trained deep learning network.

3. The method according to claim 1, further comprising:
   acquiring the retinopathy image data; and
   performing data labeling on the retinopathy image data to obtain the labeled data.

4. The method according to claim 3, further comprising:
   performing data preprocessing on the retinopathy image data to obtain preprocessed retinopathy image data,
   wherein performing the data labeling on the retinopathy image data to obtain the labeled data comprises:
      performing data labeling on the preprocessed retinopathy image data to obtain the labeled data.

5. The method according to claim 4, wherein performing the data preprocessing on the retinopathy image data comprises at least one of:
   performing image augmentation on the retinopathy image data, and
   oversampling the retinopathy image data.

6. The method according to claim 5, wherein performing the image augmentation on the retinopathy image data comprises:
   performing the image augmentation by one or more of: random tailoring, rotating, flipping, scaling, brightness adjustment, and contrast adjustment.

7. The method according to claim 1, wherein the deep learning network is an Inception-ResNet model or a GoogLeNet v3 model.

8. The method according to claim 1, wherein the loss function is:

$$L(u, v) = \Sigma_{i=\{x,y,d\}} \text{Smooth}_{L1}(u_i, v_i);$$

$$\text{Smooth}_{L1}(z) = \begin{cases} 0.5\ z^2, z < 1 \\ |z| - 0.5, z \geq 1 \end{cases};$$

wherein $v=(v_x, v_y, v_d)$ is the labeled data, $u=(u_x, u_y, u_d)$ is prediction data output by the deep learning network which corresponds to the labeled data; $v_x, v_y$ are the respective labeled eyeball center coordinates, $v_d$ is the labeled eyeball diameter; $u_x, u_y$ are the respective eyeball center coordinates output by the deep learning network, $u_d$ is the eyeball diameter output from the deep learning network, and z is the difference between the prediction data and the labeled data.

9. An electronic device, comprising:
   a processor; and
   a memory storing instructions which, when executed by the processor, cause the processor to:
      use retinopathy image data with corresponding labeled data to train a deep learning network based on a loss function, so as to obtain a trained deep learning network; and
      process retinopathy image data to be tested by using the trained deep learning network, to obtain at least one of corresponding eyeball center coordinates and an eyeball diameter.

10. The electronic device according to claim 9, wherein the instructions which, when executed by the processor, further cause the processor to:
   input the retinopathy image data to the deep learning network to obtain corresponding prediction data;
   compare the labeled data with the prediction data based on the loss function to obtain a comparison result;
   adjust parameters in the deep learning network according to the comparison result; and repeat the input, compare and adjust steps until the comparison result reaches a preset threshold, so as to obtain the trained deep learning network.

11. The electronic device according to claim 9, wherein the instructions which, when executed by the processor, further cause the processor to:
acquire the retinopathy image data; and
perform data labeling on the retinopathy image data to obtain the labeled data.

12. The electronic device according to claim 11, wherein the instructions which, when executed by the processor, further cause the processor to:
perform data preprocessing on the retinopathy image data to obtain preprocessed retinopathy image data; and
perform data labeling on the preprocessed retinopathy image data to obtain the labeled data.

13. The electronic device according to claim 12, wherein the instructions which, when executed by the processor, further cause the processor to:
perform image augmentation on the retinopathy image data; and/or
oversample the retinopathy image data.

14. The electronic device according to claim 13, wherein the instructions which, when executed by the processor, further cause the processor to:
perform the image augmentation by one or more of: random tailoring, rotating, flipping, scaling, brightness adjustment, and contrast adjustment.

15. The electronic device according to claim 9, wherein the deep learning network is an Inception-ResNet model or a GoogLeNet v3 model.

16. The electronic device according to claim 9, wherein the loss function is:

$$L(u, v) = \Sigma_{i=\{x,y,d\}} \text{Smooth}_{L1}(u_i, v_i);$$

$$\text{Smooth}_{L1}(z) = \begin{cases} 0.5\, z^2, z < 1 \\ |z| - 0.5, z \geq 1 \end{cases};$$

wherein $v=(v_x, v_y, v_d)$ is the labeled data, $u=(u_x, u_y, u_d)$ is prediction data output by the deep learning network which corresponds to the labeled data; $v_x, v_y$ are the respective labeled eyeball center coordinates, $v_d$ is the labeled eyeball diameter; $u_x, u_y$ are the respective eyeball center coordinates output by the deep learning network, $u_d$ is the eyeball diameter output from the deep learning network, and z is the difference between the prediction data and the labeled data.

17. A computer readable storage medium storing instructions, which, when executed by a processor, cause the processor to:
use retinopathy image data with corresponding labeled data to train a deep learning network based on a loss function, so as to obtain a trained deep learning network; and
process retinopathy image data to be tested by using the trained deep learning network, to obtain at least one of corresponding eyeball center coordinates and an eyeball diameter.

18. The computer readable storage medium according to claim 17, wherein the instructions which, when executed by the processor, further cause the processor to:
perform at least one of image augmentation and oversampling on the retinopathy image data to obtain preprocessed retinopathy image data; and
perform data labeling on the preprocessed retinopathy image data to obtain the labeled data.

19. The computer readable storage medium according to claim 17, wherein the deep learning network is an Inception-ResNet model or a GoogLeNet v3 model.

20. The computer readable storage medium according to claim 17, wherein the loss function is:

$$L(u, v) = \Sigma_{i=\{x,y,d\}} \text{Smooth}_{L1}(u_i, v_i);$$

$$\text{Smooth}_{L1}(z) = \begin{cases} 0.5\, z^2, z < 1 \\ |z| - 0.5, z \geq 1 \end{cases};$$

wherein $v=(v_x, v_y, v_d)$ is the labeled data, $u=(u_x, u_y, u_d)$ is prediction data output by the deep learning network which corresponds to the labeled data; $v_x, v_y$ are the respective labeled eyeball center coordinates, $v_d$ is the labeled eyeball diameter; $u_x, u_y$ are the respective eyeball center coordinates output by the deep learning network, $u_d$ is the eyeball diameter output from the deep learning network, and z is the difference between the prediction data and the labeled data.

* * * * *